United States Patent [19]

Sublette

[11] Patent Number: 5,077,208
[45] Date of Patent: Dec. 31, 1991

[54] MICROBIAL REMOVAL OF NO$_x$ FROM GASES

[75] Inventor: Kerry L. Sublette, Tulsa, Okla.

[73] Assignee: ABB Environmental Services Inc., Windsor, Conn.

[21] Appl. No.: 532,825

[22] Filed: Jun. 4, 1990

[51] Int. Cl.$^5$ .............................................. C12P 3/00
[52] U.S. Cl. .................................... 435/168; 435/170; 435/244; 435/266; 435/822; 435/874; 435/859; 435/824; 435/832
[58] Field of Search ............... 435/168, 170, 244, 266, 435/822, 874, 859, 824, 832

[56] References Cited

PUBLICATIONS

Bergey's Manual of Determinative Bacteriology, 8th ed., Buchanan, R., N. Gibbons eds. pp. 456–458, 460 (1974).

Studies on *Thiobacillus denitrificans* by Baalsrud & Baalsrud (Arch. Microbiol., 20,34 (1954)).

Intermediates of Denitrificantion in the Chemoautotroph *Thiobacillus denitrificans* by Ishaque & Aleem (Arch. Mikro 94, 269 (1973)).

Reduction of Oxidized Inorganic Nitrogen Compounds by a New Strain of *Thiobacillus denitrificans* (Arch Mikro., 103, 31 (1975)).

Primary Examiner—Lester L. Lee
Assistant Examiner—E. J. Kraus
Attorney, Agent, or Firm—Richard H. Berneike

[57] ABSTRACT

Disclosed is a process by which a gas containing nitric oxide is contacted with an anaerobic microbial culture of denitrifying bacteria to effect the chemical reduction of the nitric oxide to elemental nitrogen. The process is particularly suited to the removal of nitric oxide from flue gas streams and gas streams from nitric acid plants. *Thiobacillus dentrificians* as well as other bacteria are disclosed for use in the process.

5 Claims, 3 Drawing Sheets

MICROBIAL REMOVAL OF $NO_x$ FROM GASES

This invention was made with Government support under contract No. DE-FG22-88PC88945 awarded by the Department of Energy. The Government has certain rights in this invention.

BACKGROUND OF THE INVENTION

The present invention relates to the removal of $NO_x$ from gases such as flue gases. The gas containing the oxides of nitrogen is contacted with a culture of facultatively anaerobic bacteria capable of using nitrate as a terminal electron acceptor to effect the chemical reduction to elemental nitrogen.

A need exists for new technology for the disposal of concentrated gas streams containing oxides of nitrogen, $NO_x$ (NO and $NO_2$), as obtained from certain regenerable, dry scrubbing processes for flue gas desulfurization, such as the NOXSO process (Yeh et al, "The NOXSO Process: Simultaneous Removal of $SO_2$ and $NO_x$ from Flue Gas", paper presented at the AICHE Spring National Meeting, Houston, Tex. (March, 1987)), and the removal and disposal of $NO_x$ from more dilute gas streams such as produced by nitric acid plants.

Combustion in air inevitably produces oxides of nitrogen due to the reaction at high temperatures of elemental nitrogen or fuel nitrogen with oxygen. Roughly 90-95% of the oxides of nitrogen emitted in combustion processes is in the form of nitric oxide (NO). The remainder is predominately nitrogen dioxide ($NO_2$). In the atmosphere NO is converted in time to $NO_2$. Since NO and $NO_2$ generally coexist in varying proportions in flue gases and in the atmosphere, they are frequently lumped together under the generic formula $NO_x$.

In urban metropolitan areas where $NO_x$ emission sources are concentrated, $NO_x$ reacts with hydrocarbons in the atmosphere in photochemical reactions to produce smog. The chemical components of smog, particularly organic peroxy nitrates and ozone have a direct adverse effect on human health and plant life.

$NO_x$ emissions may be controlled in basically two ways. First, emissions may be reduced by decreasing the residence time of combustion gases at peak flame temperatures (high temperature favors $NO_x$ formation) and reducing the availability of oxygen. However, these measures can be expensive to implement and, in the latter case, result in increased emissions of carbon monoxide, another serious pollutant. Where combustion control is not feasible, $NO_x$ must be removed from the cooled flue gases before they are released into the atmosphere. However, flue gas cleaning for $NO_x$ removal has been severely limited by the low reactivity of nitrogen oxides and the large volume of gas to be treated at most stationary combustion sources.

*Thiobacillus denitrificans* is a strict autotroph and facultative anaerobe first described in detail by Baalsrud & Baalsrud (Arch. Microbiol., 20, 34 (1954)). Under anaerobic conditions, nitrate may be used as a terminal electron acceptor with reduction to elemental nitrogen. Thiosulfate, elemental sulfur and sulfide may be used as energy sources with oxidation to sulfate. Nitric oxide (NO) has been shown to be an intermediate in the reduction of nitrate to elemental nitrogen in *T. denitrificans*. Ishaque & Aleem (Arch. Mikro, 94, 269 (1973)) and Baldensparger & Garcia (Arch. Mikro., 103, 31 (1975)) have demonstrated that whole cells of *T. denitrificans* will catalyze the reduction of nitric oxide to elemental nitrogen with a concomitant oxidation of thiosulfate (electron donor). However, these experiments utilized "resting cells"; that is, the cells were not actively growing and reproducing. Since nitric oxide reduction in *T. denitrificans* would be directly linked to the energy metabolism of the cell, the highest specific activity for NO reduction should occur when cells are actively growing and reproducing.

SUMMARY OF INVENTION

The current invention consists of a process by which a gas containing nitric oxide is contacted with an anaerobic microbial culture containing one or more denitrifying bacteria to effect the chemical reduction of nitric oxide (NO) to elemental nitrogen. The bacteria are in a suitable medium conducive to cell viability and growth but lacking any source of terminal electron acceptor except nitric oxide. The current invention is particularly well suited for the disposal of concentrated streams of $NO_x$ (NO and $NO_2$) as may be obtained from certain regenerable, dry scrubbing processes for flue gas desulfurization, such as the NOXSO process, and the removal and disposal of $NO_x$ from more dilute gas streams such as produced by nitric acid plants.

Although the invention will be described with reference to the use of *Thiobacillus denitrificans*, other facultatively anaerobic bacteria capable of using nitrate as a terminal electron acceptor with reduction to elemental nitrogen can be used. Examples of other bacteria include but are not limited to species of the genera Pseudomonas, Paracoccus, Micrococcus, Rhodopseudomonas, Rhodobacter, Alcaliqenes, Achromobacter, and Bacillus.

DESCRIPTION OF PREFERRED EMBODIMENT

It has been discovered that nitric oxide will support the anaerobic growth of *T. denitrificans* as a terminal electron acceptor. The following description of the preferred embodiment of the invention describes the best means known to apply the current invention and the results of the application of the invention to the removal and disposal of nitric oxide from a gas stream.

*T. denitrificans* (ATCC 23642) was obtained from the American Type Culture Collection (Rockville, Md.). In a typical batch experiment the organism was grown in a B. Braun Biostat M fermenter (culture volume 1.4 l) in the thiosulfate medium described in Table 1.

TABLE 1

| Thiosulfate maintenance medium for *Thiobacillus denitrificans*. | |
|---|---|
| Component | Per Liter |
| $Na_2HPO_4$ | 1.2 g |
| $KH_2PO_4$ | 1.8 g |
| $MgSO_4.7H_2O$ | 0.4 g |
| $NH_4Cl$ | 0.5 g |
| $CaCL_2$ | 0.03 g |
| $MnSO_4$ | 0.02 g |
| $FeCl_3$ | 0.02 g |
| $NaHCO_3$ | 1.0 g |
| $KNO_3$ | 5.0 g |

TABLE 1-continued
Thiosulfate maintenance medium for *Thiobacillus denitrificans*.

| Component | Per Liter |
| --- | --- |
| $Na_2S_2O_3$ | 10.0 g |
| Trace metal solution | 15.0 mL |
| Mineral Water | 50.0 mL |

In this medium, thiosulfate is the energy source, nitrate is the terminal electron acceptor, carbon dioxide or bicarbonate is the carbon source and ammonium ion ($NH_4^+$) the source of reduced nitrogen. The culture was incubated at 30° C. (with pH control at 7.0) to a cell density of approximately $5 \times 10^8$ cells/ml. At this time, cells were harvested aseptically by centrifugation at $5000 \times g$ for 10 min and resuspended in the same medium without nitrate. A gas feed of 0.48% NO, 5% $CO_2$ and the balance nitrogen was then initiated at 10.5 l/hr corresponding to a molar NO feed rate of 2.0 mmoles/hr. An agitation rate of 800-900 rpm was used. Cumulative outlet gas flow was measured with a Precision Wet Test Meter. The culture medium and outlet gas were sampled periodically as the cultures were maintained on a NO feed for up to 7 days.

Thiosulfate was determined in culture medium samples by titration with standard iodine (Meites, *Handbook of Analytical Chemistry*, McGraw-Hill, N.Y. (1963)). Biomass protein was determined by sonication to break cells followed by spectrophotometric analysis by the micro-Folin method (Lowry et al. J. Biol. Chem., 193, 265 (1951)). Ammonium ion was determined by the Nessler's test without distillation (American Public Health Association, *Standard Methods for the Examination of Water & Wastewater*, 14th Ed., APHA, NY (1976)). Nitrite was determined by the diazotization method using chromatropic acid and sulfanilic acid (American Public Health Association, *Standard Methods for the Examination of Water & Wastewater*, 14th Ed., APHA, NY (1976)). NO in the outlet gas was determined by Gastech Analyzer tubes (Gastec Corp., Yokohama, Japan). These tubes had a range of 0-200 ppm NO and an accuracy as given by the manufacturer of $\pm 25\%$.

Figure 1:
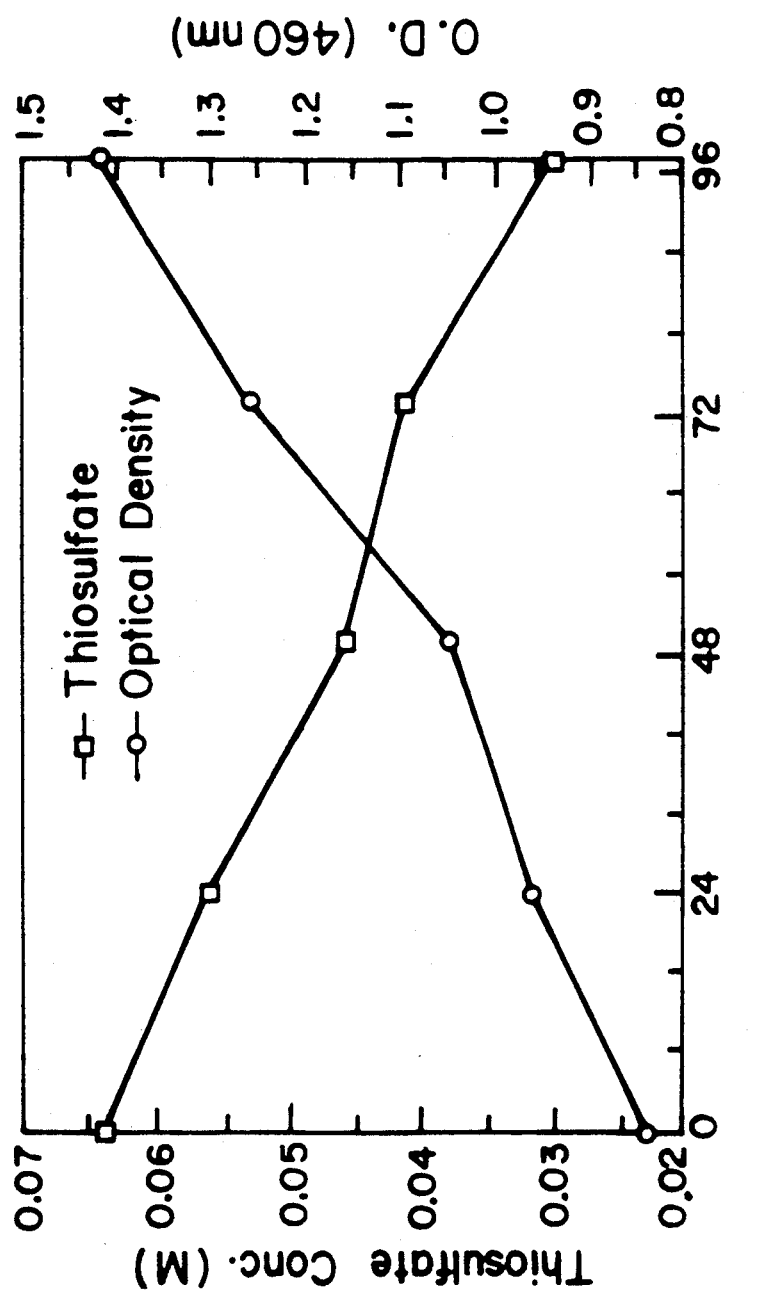
FIGS. 1 and 2 are graphs showing the reduction in thiosulfate and ammonium ions and the increase in optical density and biomass protein over a period of time employing the present invention.
Figure 2:
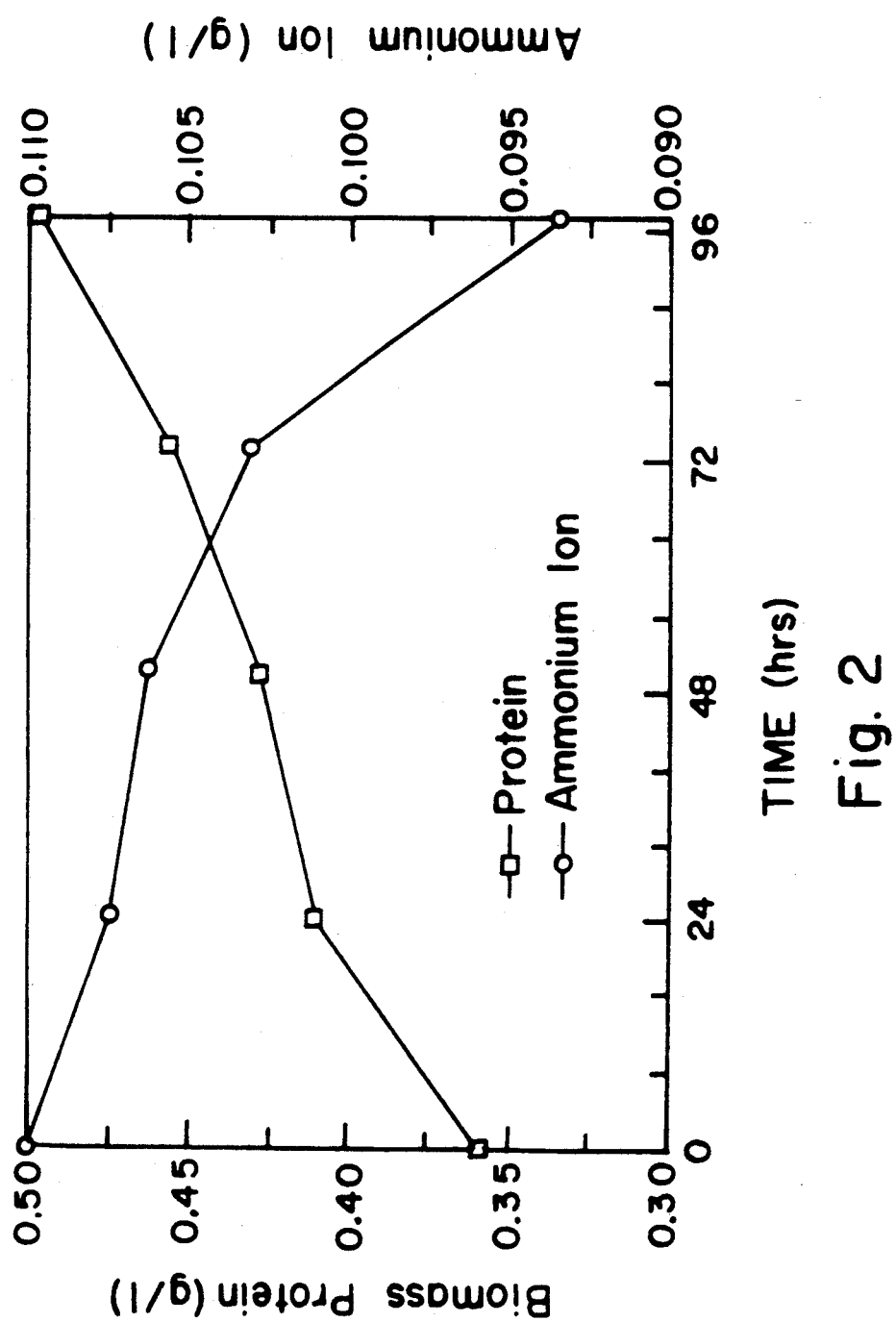

When NO introduced into *T. denitrificans* cultures previously grown on thiosulfate with nitrate as the terminal electron acceptor, the NO content of the feed gas was typically reduced to 100-200 ppm in the outlet gas and remained at this level throughout the course of the experiment. As NO was removed from the feed gas the concentrations of thiosulfate and ammonium ion were reduced in the culture medium with a corresponding increase in optical density and biomass protein as shown in FIGS. 1 and 2. Growth of *T. denitrificans* on thiosulfate as an energy source and NO as a terminal electron acceptor is clearly indicated. In control experiments without biomass, NO broke through almost immediately at concentrations comparable to the feed gas and no oxidation of thiosulfate was observed. Nitrite accumulated in the absence of biomass; however, little or no nitrite was detected in the culture medium in the presence of *T. denitrificans*.

In a typical experiment the oxidation of 45.8 mmoles of thiosulfate was accompanied by the reduction of 190.1 mmoles NO, the utilization of 4.7 mmoles of $NH_4^+$ and the production of 188 mg of biomass protein. The $NO/S_2O_3^{-2}$ ratios for four duplicate experiments given in Table 2. The average ratio was 4.1. The purely chemical reduction of NO by $S_2O_3^{-2}$ would be given by $$S_2O_3^{-2} + 4NO \; 2 \; SO_4^{-2} + 2 \; N_2$$

Therefore the chemical reduction of NO by $S_2O_3^{-2}$ has a stoichiometry of 4 ($NO/S_2O_3^{-2}$). Given that NO supports the growth of *T. denitrificans* as a terminal electron acceptor, a $NO/S_2O_3^{-2}$ ratio of less than 4 would be expected since some electrons derived from $S_2O_3^{-2}$ would be used as reducing equivalents to support biosynthesis (growth). The discrepancy between this analysis and the data presented in Table 2 is likely due to errors in gas analysis for NO.

TABLE 2
Stoichiometry of NO Reduction by *T. denitrificans* with Thiosulfate as Electron Donor

| Exp. no. | $NO/S_2O_3^{-2}$ |
| --- | --- |
| 1 | 3.6 |
| 2 | 4.2 |
| 3 | 4.4 |
| 4 | 4.2 |
| | 4.1 average |

It has been clearly demonstrated that nitric oxide will support the growth of *T. denitrificans* as a terminal electron acceptor with thiosulfate as the energy source (electron donor). The low solubility of NO in water resulted in incomplete removal of NO from the feed gas in one contacting stage. However, up to 96% removal of NO was observed. Complete removal could be achieved with multiple stage contacting.

Figure 3:
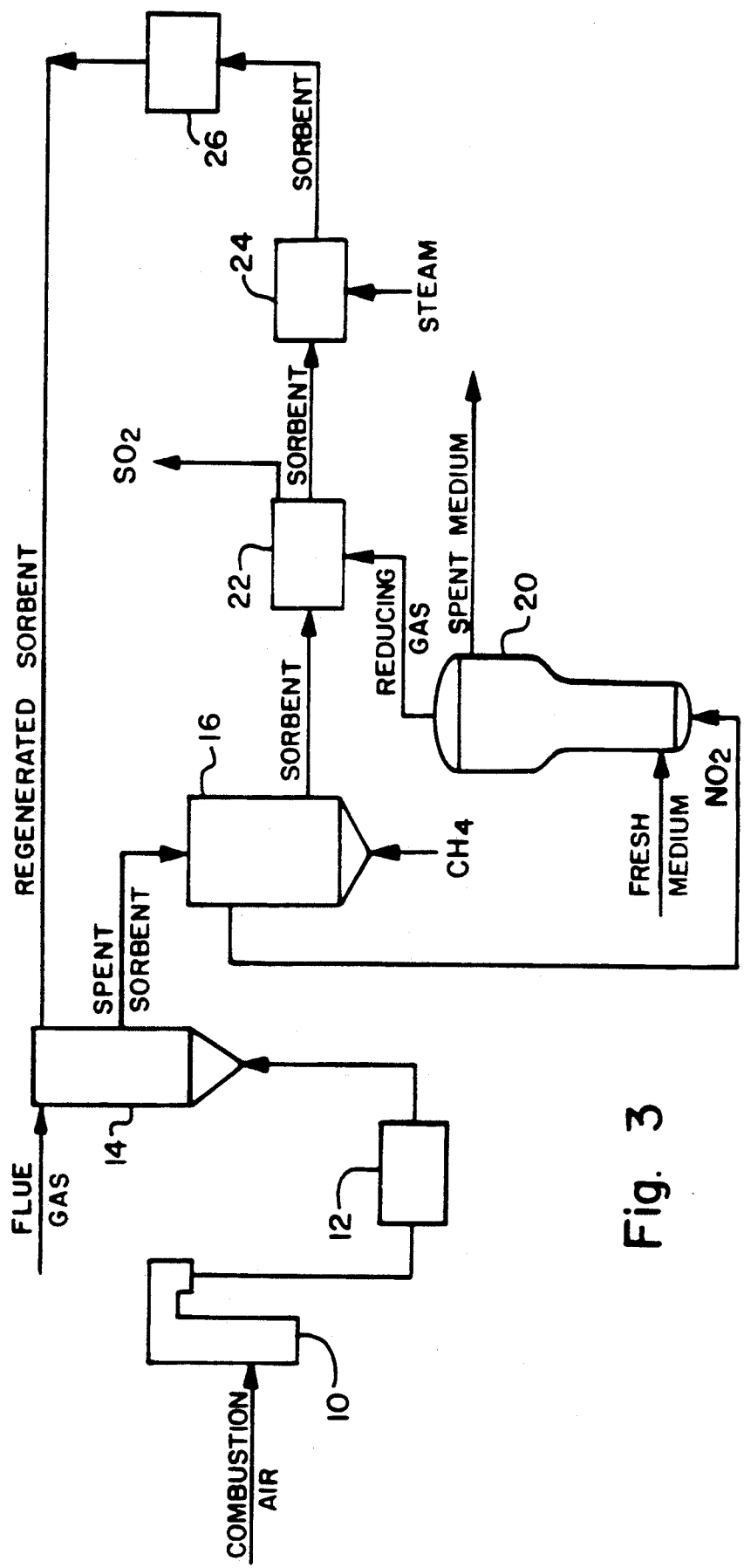
FIG. 3 is a schematic flow diagram illustrating the present invention in the removal of $NO_x$ from a gas stream.

Although thiosulfate has been described as the energy source for *T. denitrificans*, the current invention is not limited to thiosulfate. Elemental sulfur and inorganic soluble sulfides ($H_2S$, $HS^-$, $S^{-2}$) could be used as the energy source within the concept of the current invention. The invention is also not limited to the wild-type strain of *T. denitrificans* (ATCC 23642) used in these experiments. Any wild-type strain of *T. denitrificans* and any mutant thereof could be used within the context of the present invention, as well as the denitrifying species of the previously mentioned genera Pseudomonas, Paracoccus, Micrococcus, Rhodopseudomonas, Rhodobacter, Alcaliqenes, Achromobacter, and Bacillus. Referring now to FIG. 3, the present invention is illustrated in the context of a combustion process in a boiler 10. In this particular example, the NOXSO process previously referred to is used for illustration. The flue gas from the combustion process containing the nitric oxide is cooled at 12 to a temperature appropriate for the following adsorbtion process, typically to about 120° C. The cooled gas from 12 is fed to the fluidized bed adsorber 14 where the $NO_x$ and $SO_2$ are both adsorbed by an adsorbant which consists of $Na_2CO_3$ deposited on the surface of an alumina substrate.

The $Na_2CO_3$ deposit is unstable in the presence of alumina at between 400° and 700° C. In this temperature range, sodium combines with alumina to form sodium aluminate ($NaAlO_2$). $NaAlO_2$ adsorbs $SO_2$ and $NO_x$ simultaneously to form sodium sulfate ($Na_2SO_4$), sodium nitrite ($NaNO_2$) and sodium nitrate ($NaNO_3$). Both sodium and alumina chemisorb $SO_2$ from the flue gas. It has also been demonstrated that $NO_x$ chemisorbs on Lewis acid sites (aluminum ions) on gamma-alumina.

The regeneration of active adsorption sites in the NOXSO process is accomplished first by heating the spent sorbent to about 600° C. at 16. The product of chemisorption of $NO_x$ is unstable at temperature above 400° C. By heating the sorbent to the sulfur regeneration temperature of 600° C., a concentrated stream 18 of $NO_x$ is generated. This concentrated stream 18 of $NO_x$ is then treated in the bioreactor 20 according to the present invention. The subsequent treatment of the adsorbent from the heater 16 is in the regenerator 22 with the reducing gas from the bioreactor containing the nitrogen and methane to yield a mixture of $SO_2$ and $H_2S$. The sulfide produced remains on the sorbent after treatment and is subsequently removed by treatment with steam at 24 to yield further $SO_2$ and $H_2S$. The $H_2S$ thus generated may be burned to produce a concentrated stream of $SO_2$ for the formation of sulfuric acid. Alternatively, the mixture of $SO_2$ and $H_2S$ obtained from the regeneration process can be used as feed to a Claus reactor to form elemental sulfur. The regenerated adsorbent is then recycled to the fluidized bed adsorber 14 through the cooler 26.

What is claimed is:

1. A process for converting nitric oxide in a gas stream to elemental nitrogen comprising contacting said gas stream under anaerobic conditions with a slurry containing a denitrifying bacterium capable of converting said nitric oxide to elemental nitrogen and a culture medium containing an energy source for said bacterium and adapted to maintain the viability and growth of said bacterium and wherein said slurry contains essentially no source of terminal electron acceptor except said nitric oxide whereby said nitric oxide is reduced to elemental nitrogen by said bacteria.

2. A process as claimed in claim 1 wherein said denitrifying bacteria is *Thiobacillus denitrificans*.

3. A process as claimed in claim 2 in which the culture medium contains thiosulfate, ammonium ion, a phosphate buffer, a carbonate or biocarbonate and trace amounts of iron, magnesium, manganese, and calcium.

4. A process as claimed in claim 2 in which said energy source in the culture medium is a sulfide.

5. A process as claimed in claim 2 in which said energy source in the culture medium is elemental sulfur.

* * * * *